United States Patent [19]

Ose et al.

[11] 4,341,770

[45] Jul. 27, 1982

[54] METHOD OF CONTROLLING UREAPLASMA INFECTIONS

[75] Inventors: Earl E. Ose, Greenfield; Herbert A. Kirst, Indianapolis, both of Ind.

[73] Assignee: Eli Lilly and Company, Indianapolis, Ind.

[21] Appl. No.: 255,575

[22] Filed: Apr. 20, 1981

[51] Int. Cl.$^3$ .................... A61K 31/71; A61K 31/70
[52] U.S. Cl. .................................... 424/181; 424/180
[58] Field of Search ............................. 424/180, 181

[56] References Cited

U.S. PATENT DOCUMENTS

| | | | |
|---|---|---|---|
| 3,178,341 | 4/1965 | Hamill et al. | 167/65 |
| 3,326,759 | 6/1967 | Hamill et al. | 167/65 |
| 3,344,024 | 9/1967 | Whaley et al. | 167/65 |
| 3,459,853 | 8/1969 | Gorman et al. | 424/121 |
| 3,769,273 | 10/1973 | Massey | 260/210 |
| 4,234,690 | 11/1980 | Weinstein et al. | 435/119 |
| 4,252,898 | 2/1981 | Nash et al. | 435/76 |

OTHER PUBLICATIONS

Kishima et al., Chem. Abst. vol. 92 (1980), p. 34976n.
Kishima et al., Research in Veterinary Science, vol. 27 (1979), pp. 218-222.
K. Fujisawa et al., "Studies on Cirramycin A$_1$. II Biological Activity of Cirramycin A$_1$," *J. Antibiotics* 22(2), 65-70 (1969).
H. Tsukiura et al., "Studies on Cirramycin A$_1$. IV Derivatives of Cirramycin A$_1$," *J. Antibiotics* 22(3), 100-105 (1969).
T. Furumai et al., "Macrolide Antibiotics M-4365 Produced by *Micromonospora*. I. Taxonomy, Production, Isolation, Characterization and Properties," *J. Antibiotics* 30, 443-449 (1977).
T. Yamaguchi et al., "Macrolide Antibiotics M-4365 Produced by *Micromonospora* III. In Vitro Antimicrobial Activity of Antibiotic M-4365 G$_2$ (De-epoxy Rosamicin)", *J. Antibiotics* 31, 433-440 (1978).
S. Omura et al., "Antimycoplasma Activities of Macrolide Antibiotics," *J. Antibiotics* 25 (2), 105-108 (1972).
T. Matsuoka et al., "Orally Administered Tylosin for the Control of Pneumonia in Neonatal Calves," *Veterinary Record* 107, 149-151 (1980).

*Primary Examiner*—Sam Rosen
*Attorney, Agent, or Firm*—Nancy J. Harrison; Arthur R. Whale

[57] ABSTRACT

Method of controlling Ureaplasma infections which comprises administering to an infected or susceptible warm-blooded animal an effective amount of 5-0-mycaminosyl tylonolide or a pharmaceutically acceptable acid addition salt thereof.

7 Claims, No Drawings

METHOD OF CONTROLLING UREAPLASMA INFECTIONS

SUMMARY OF THE INVENTION

This invention relates to a method of controlling Ureaplasma infections. In particular, this invention relates to the method of controlling Ureaplasma infections which comprises administering to an infected or susceptible warm-blooded animal 5-O-mycaminosyl tylonolide (OMT) or a physiologically acceptable acid addition salt of OMT.

Ureaplasma infections cause serious problems in animals. Ureaplasma species are implicated as a primary agent of pneumonia in calves. In cattle and sheep they are considered a cause of fertility problems and abortion. *Ureaplasma urealyticum* has been associated with non-gonococcal urethritis and infertility in men, spontaneous abortions in women and pneumonia in babies.

The genus Ureaplasma is a member of the family Mycoplasmataceae, which is in the order Mycoplasmatales, which is in the class Mollicutes. The genus Mycoplasma is the other member of the family Mycoplasmataceae. Ureaplasma species are faster growing than Mycoplasma species. Ureaplasma species have a generation time of less than one hour. In addition, Ureaplasma species are resistant to some important antibiotics such as lincomycin. Thus, new methods of controlling Ureaplasma infections are continually being sought.

DETAILED DESCRIPTION OF THE INVENTION

We have discovered that OMT exhibits an unexpectedly high activity against Ureaplasma species. More particularly, we have discovered that OMT is effective in vivo as well as in vitro against Ureaplasma species.

OMT was described by Marvin Gorman and Robert B. Morin in U.S. Pat. No. 3,459,853 issued Aug. 5, 1969, which taught that OMT inhibited gram-positive bacteria. OMT was later found to have the structure shown in formula 1:

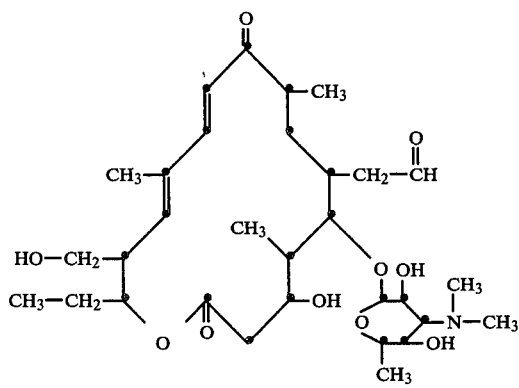

OMT can be prepared by hydrolysis of tylosin, desmycosin, macrocin or lactenocin under mildly acidic conditions as described in U.S. Pat. No. 3,459,853. Another method of preparing OMT is described by Richard H. Baltz, Gene M. Wild, and Eugene T. Seno in their copending application entitled DEMYCINOSYL-TYLOSIN AND PROCESS FOR ITS PRODUCTION, Ser. No. 156,854, filed June 12, 1980. This method comprises preparing OMT by mild acid hydrolysis of 23-demycinosyltylosin (DMT). The structure of DMT is shown in formula 2:

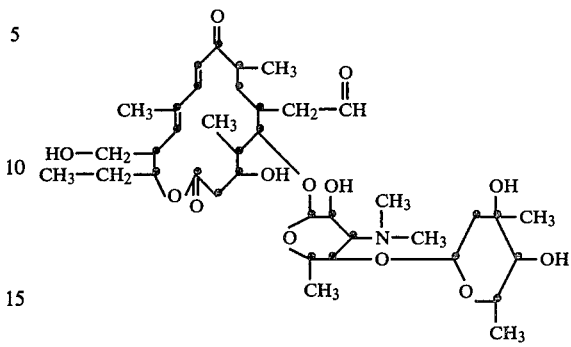

DMT is prepared by fermentation of *Streptomyces fradiae* NRRL 12170 under submerged aerobic conditions until a substantial level of antibiotic activity is produced. DMT can be extracted from basified broth filtrate with polar organic solvents and can be further purified by extraction, chromatography, and/or crystallization.

The DMT-producing strain of *Streptomyces fradiae* has been deposited and made part of the stock culture collection of the Northern Regional Research Center, Agricultural Research, North Central Region, 1815 North University Street, Peoria, Ill., 61604, from which it is available to the public under the accession number NRRL 12170.

OMT is prepared from DMT by mild acid hydrolysis. Appropriate solutions having a pH of about four or below can be used to accomplish the hydrolysis. Temperatures of about 20° to about 100° C. can be used in this method. The reaction time needed to carry out the hydrolysis varies, depending upon the pH of the reaction mixture and the temperature used. At higher pH levels the reaction rate is slower, and at higher temperatures the reaction rate is faster. The reaction is carried out by treating DMT with a mild acid solution for a time sufficient to effect removal of the mycarosyl group to give OMT.

Alternatively, and sometimes preferably, OMT can be prepared by treating DMT in the fermentation broth in which it is produced, using mild acidic conditions as described above for a time sufficient to convert the DMT to OMT. OMT thus prepared can be isolated from the fermentation broth using techniques known in the art.

In carrying out the method of this invention, OMT or a pharmaceutically acceptable acid addition salt of OMT is administered parenterally to an animal infected with or susceptible to Ureaplasma infection. The dose used to control Ureaplasma infections will vary with the severity of the infection and the age, weight, and condition of the animal. The total dose required for several days protection will generally, however, be in the range of from about 10 to about 300 mg/kg and preferably will be in the range of from about 25 to about 175 mg/kg. Protection for up to about seven days can be provided by a single injection; the exact length of protection will depend upon the dose given. The total dose can also be divided into smaller doses given at intervals, such as once daily for about four to seven days. Obviously, other suitable dosage regimens can be constructed.

The compounds of this invention may be formulated for parenteral administration by methods recognized in the veterinary pharmaceutical art. Effective injectable compositions containing these compounds may be in either suspension or solution form. In the preparation of suitable formulations it will be recognized that, in general, the water solubility of OMT acid addition salts is greater than that of OMT base. Similarly, OMT base is more soluble in dilute acids or in acidic solutions than in neutral or basic solutions.

In the solution form the compound is dissolved in a physiologically acceptable vehicle. Such vehicles comprise a suitable solvent, preservatives such as benzyl alcohol, if needed, and buffers. Useful solvents include, for example, water and aqueous alcohols, glycols, and carbonate esters such as diethyl carbonate. Such aqueous solutions contain, in general, no more than 50% of the organic solvent by volume.

Injectable suspension compositions employ a liquid suspending medium, with or without adjuvants, as a vehicle. The suspending medium can be, for example, aqueous polyvinylpyrrolidone, inert oils such as vegetable oils or highly refined mineral oils, or aqueous carboxymethylcellulose.

Suitable physiologically acceptable adjuvants are necessary to keep the compound suspended in suspension compositions. The adjuvants may be chosen from among thickeners such as carboxymethylcellulose, polyvinylpyrrolidone, gelatin, and the alginates. Many surfactants are also useful as suspending agents. Lecithin, alkylphenol polyethylene oxide adducts, naphthalenesulfonates, alkylbenzenesulfonates, and the polyoxyethylene sorbitan esters are useful suspending agents.

Many substances which affect the hydrophilicity, density, and surface tension of the liquid suspending medium can assist in making injectable suspensions in individual cases. For example, silicone antifoams, sorbitol, and sugars can be useful suspending agents.

The compounds of this invention exhibit unexpectedly high activity against Ureaplasma species both in vitro and in vivo. For example, in the conventional broth-dilution assay, OMT had minimal inhibitory concentrations (MIC's) against four isolates of Ureaplasma as shown in Table I.

TABLE I

| Activity of OMT Against Ureaplasma Isolates | |
|---|---|
| Ureaplasma Isolate | MIC (mcg/ml) |
| 763T-2 | 0.78 |
| 765T-3 | 1.56 |
| 773T-2 | 1.56 |
| 779T-3 | 1.56 |

Example one illustrates the useful in vivo activity of OMT against Ureaplasma. In the example OMT (free base) was administered in an aqueous propylene glycol solution, and non-medicated water and feed were provided to the animals ad libitum.

EXAMPLE 1

Treatment of Pneumonia in Calves With OMT

OMT was evaluated in calves for the treatment of naturally occurring pneumonia. Calves were purchased and transported to Lilly Research Laboratories, Greenfield, Indiana. The calves were weighed, bled, identified with eartags and allotted into pens soon after arrival. Rectal temperatures were taken and clinical observations were made daily.

Calves were put on test at the first signs of respiratory disease which included ocular and nasal discharges, pyrexia and/or depression.

Treated calves were injected intramuscularly with OMT in an aqueous propylene glycol vehicle. The treatment doses evaluated were 12.5 mg/kg and 25 mg/kg once a day for five days. Control calves were treated with placebo. There were 10 calves per group. Calves that died were examined at necropsy for lesions indicative of pneumomia. Surviving calves were killed seven days after the last treatment and examined for lesions at necropsy.

The temperature averages of the calves in the 25 mg/kg- and 12.5 mg/kg-treatment groups were lowered to normal by the second day of treatment. In comparison, the average temperatures of nonmedicated controls remained above 40° C. (104° F.) for 10 days after they were put on test. Scours and ocular discharge were reduced in the treated calves at both OMT dose levels. Six of ten placebo-treated calves died, whereas only two of ten in each of the OMT-treated groups died. At necropsy extensive pathologic lesions in lung tissue were indicative of a severe pneumonia in the calves that died during the trial.

The Pasteurella species associated with this pneumonia was effectively controlled by both OMT treatments. The method of controlling Pasteurella infections with OMT is discussed in our copending case entitled METHOD OF CONTROLLING PASTEURELLA INFECTIONS, Ser. No. 255,577, filed herewith this even date.

A Ureaplasma species which was isolated from lung tissue of calves treated with placebo and 12.5 mg OMT/kg was not isolated from calves treated with 25 mg OMT/kg. Thus, treatment with 25 mg/kg of OMT eliminated the Ureaplasma species from the animals in this group.

EXAMPLE 2

Prevention of Pneumonia in Calves With OMT

OMT was evaluated in calves for the prevention and control of naturally occurring pneumonia. Calves were purchased and transported to Lilly Research Laboratories, Greenfield, Ind. Soon after arrival the calves were weighed, bled, identified with eartags and allotted into pens. There were 19 calves in the OMT-treated group and 19 calves in the nontreated control group.

OMT was prepared as an injectable in an aqueous propylene glycol vehicle. The treated calves were each injected subcutaneously with 35 mg/lb (77 mg/kg) of OMT within a day after arrival. At this dose and route of administration, the drug was expected, based on blood level studies, to persist for seven days in the treated calves. The calves were each retreated with the same dose seven days later. Rectal temperatures were taken and clinical observations were made daily. Calves that died were examined at necropsy for lesions indicative of pneumonia.

During the 14-day observation period following the first injection the average temperatures were lower in treated calves than in the non-medicated controls. Treated calves had less severe nasal and ocular discharges and less severe scours. Calves on treatment also appeared more alert and in better condition than the controls. The cumulative mortality for the first 14 days was as follows:

| | CUMULATIVE MORTALITY RATE | | | | | | | | | | | | | |
|---|---|---|---|---|---|---|---|---|---|---|---|---|---|---|
| | Days on Test | | | | | | | | | | | | | |
| Group* | 1 | 2 | 3 | 4 | 5 | 6 | 7 | 8 | 9 | 10 | 11 | 12 | 13 | 14 |
| Control | 0 | 0 | 0 | 1 | 3 | 5 | 5 | 5 | 9 | 11 | 13 | 14 | 14 | 15 |
| OMT | 0 | 0 | 0 | 0 | 0 | 0 | 0 | 0 | 0 | 0 | 0 | 0 | 2 | 3 |

*19 Calves per Group

The mortality data indicated that treatment with OMT was very effective in preventing death of calves due to a severe pneumonia. The naturally occurring pneumonia in these calves was judged to be severe based upon the high mortality rate of non-medicated controls. Additionally, all of the calves that died were examined at necropsy; of these, 14 of the 15 control calves and the 3 treated calves had extensive pathologic lesions indicative of severe pneumonia.

EXAMPLE 3

Preparation of OMT from DMT

A. Shake-flask Fermentation of DMT

A lyophilized pellet of *Streptomyces fradiae* NRRL 12170 is dispersed in 1–2 ml of sterilized water. A portion of this solution (0.5 ml) is used to inoculate a vegetative medium (150 ml) having the following composition:

| Ingredient | Amount (%) |
|---|---|
| Corn steep liquor | 1.0 |
| Yeast extract | 0.5 |
| Soybean grits | 0.5 |
| CaCO$_3$ | 0.3 |
| Soybean oil (crude) | 0.45 |
| Deionized water | 97.25 |

Alternatively, a vegetative culture of *S. fradiae* NRRL 12170, preserved in 1-ml volumes in liquid nitrogen, is rapidly thawed and used to inoculate the vegetable medium. The inoculated vegetative medium is incubated in a 500-ml Erylenmeyer flask at 29° C. for about 48 hours on a closed-box shaker at 300 rpm.

This incubated vegetative medium (0.5 ml) is used to inoculate 7 ml of a production medium having the following composition:

| Ingredient | Amount (%) |
|---|---|
| Beet molasses | 2.0 |
| Corn meal | 1.5 |
| Fish meal | 0.9 |
| Corn gluten | 0.9 |
| NaCl | 0.1 |
| (NH$_4$)$_2$HPO$_4$ | 0.04 |
| CaCO$_3$ | 0.2 |
| Soybean oil (crude) | 3.0 |
| Deionized water | 91.36 |

The inoculated fermentation medium is incubated in a 50-ml bottle at 29° C. for about 6 days on a closed-box shaker at 300 rpm.

B. Tank Fermentation of DMT

In order to provide a larger volume of inoculum, 1200 ml of incubated vegetable medium, prepared in a manner similar to that described in section A, is used to inoculate 250 gallons of a second-stage vegetative growth medium having the following composition:

| Ingredient | Amount (%) |
|---|---|
| Corn steep liquor | 1.0 |
| Soybean oil meal | 0.5 |
| Yeast extract | 0.5 |
| CaCO$_3$ | 0.3 |
| Soybean oil (crude) | 0.5 |
| Lecithin (crude) | 0.015 |
| Water | 97.185 |
| Adjust pH to 8.5 with 50% NaOH solution. | |

This second-stage vegetative medium is incubated in a 350-gallon tank for about 48 hours at 28° C., with adequate aeration and agitation.

Incubated second-stage medium (144 gallons) thus prepared is used to inoculate 1000 gallons of sterile production medium having the following composition:

| Ingredient | Amount (%) |
|---|---|
| Fish meal | 0.875 |
| Corn meal | 1.5 |
| Corn gluten | 0.875 |
| CaCO$_3$ | 0.2 |
| NaCl | 0.1 |
| (NH$_4$)$_2$HPO$_4$ | 0.04 |
| Beet molasses | 2.0 |
| Soybean oil (crude) | 3.0 |
| Lecithin | 0.09 |
| Water | 91.32 |
| Adjust pH to 7.2 with 50% NaOH solution. | |

The inoculated production medium is allowed to ferment in a 1600-gallon tank for 8 to 9 days at a temperature of 28° C. The fermentation medium is aerated with sterile air to keep the dissolved oxygen level between about 30% and 50% and is stirred with conventional agitators at about 250 rpm.

C. Isolation of DMT

Harvested whole broth (3800 L), obtained as described in Section B, is filtered, using a filter aid. The mycelial cake is washed with water; this water wash is added to the filtrate.

The pH of the filtrate is adjusted to pH 9.2, using a 50% aqueous solution of sodium hydroxide (9.5 L). The filtrate is extracted with ethyl acetate (2000 L). Deionized water (450 L) and sodium phosphate monobasic (6.4 kg) are added to the ethyl acetate extract with thorough mixing. The pH of this mixture is adjusted from about pH 6.0 to pH 4.35, using a phosphoric acid solution (3300 ml; 2 parts water to one part phosphoric acid). The aqueous phase is separated. The pH of the enriched aqueous phase is adjusted to pH 6.5 using a 50% aqueous sodium hydroxide solution (700 ml).

The resulting solution is concentrated to a volume of about 225 L under vacuum. The pH of the concentrated solution is adjusted to pH 9.2 by the addition of 10% aqueous sodium hydroxide (16 L). The resulting basic solution is permitted to stand overnight. The crystals which form are separated by filtration, washed with deionized water (50 L), and dried to give about 8.6 kg of product. The product thus obtained can be recrystallized from acetone-water.

D. Preparation of OMT

DMT, prepared as described in Section C, is dissolved in a dilute hydrochloric acid solution (final pH 1.8). The resulting solution is allowed to stand for 24 hours at room temperature and then is adjusted to pH 9.0 by the addition of sodium hydroxide. This basic solution is extracted with ethyl acetate, dichloromethane or chloroform. The extract is evaporated under vacuum to give OMT.

EXAMPLE 4

Alternate Preparation of OMT from DMT

OMT is prepared from DMT by treating the DMT in the fermentation broth in which it is produced with mild acid as described in Section D of Example 3. Isolation of the OMT is accomplished by a procedure similar to that described for DMT in Section C of Example 3.

EXAMPLE 5

OMT Injectable Formulations (A) OMT base is added to propylene glycol. Water and benzyl alcohol are added so that the solution contains 50% (by volume) propylene glycol, 4% (by volume) benzyl alcohol and 200 mg/ml of OMT base.

(B) An OMT solution is prepared as described in Section A except that the solution contains 50 mg/ml of OMT base.

(C) An OMT solution is prepared as described in Section A except that the solution contains 350 mg/ml of OMT.

(D) An OMT solution is prepared as described in Section A except that the solution contains 500 mg/ml of OMT tartrate.

(E) An OMT suspension is prepared by adding finely ground OMT to carboxymethyl cellulose with thorough mixing so that the suspension contains 200 mg of OMT base per ml of suspension.

We claim:

1. A method for controlling Ureaplasma infections which comprises administering to an infected or susceptible animal selected from the group consisting of humans, cattle or sheep an amount effective for treating the Ureaplasma infection of a composition comprising 5-O-mycaminosyl tylonolide or a pharmaceutically acceptable acid addition salt of 5-O-mycaminosyl tylonolide and a suitable pharmaceutical vehicle.

2. The method of claim 1 wherein the compound is 5-O-mycaminosyl tylonolide.

3. The method of claim 1 wherein the compound is 5-O-mycaminosyl tylonolide tartrate.

4. The method of claim 1 wherein the compound is 5-O-mycaminosyl tylonolide phosphate.

5. The method of claim 1, 2, 3 or 4 wherein the vehicle is aqueous propylene glycol.

6. The method of claim 1, 2, 3 or 4 wherein the composition is administered as a single injection.

7. The method of claim 1, 2, 3 or 4 wherein divided doses of the composition are administered in a series of injections.

* * * * *